US010561316B2

(12) United States Patent
Freeman et al.

(10) Patent No.: US 10,561,316 B2
(45) Date of Patent: Feb. 18, 2020

(54) PUPILLOMETRY BASED CARDIOPULMONARY THERAPY

(71) Applicant: ZOLL Medical Corporation, Chelmsford, MA (US)

(72) Inventors: Gary A. Freeman, Waltham, MA (US); Naveed Zaidi, Shrewsbury, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 168 days.

(21) Appl. No.: 15/561,109

(22) PCT Filed: Mar. 8, 2016

(86) PCT No.: PCT/US2016/021353
§ 371 (c)(1),
(2) Date: Sep. 25, 2017

(87) PCT Pub. No.: WO2016/160286
PCT Pub. Date: Oct. 6, 2016

(65) Prior Publication Data
US 2018/0116510 A1 May 3, 2018

Related U.S. Application Data

(60) Provisional application No. 62/139,460, filed on Mar. 27, 2015.

(51) Int. Cl.
A61B 3/14 (2006.01)
A61H 31/00 (2006.01)
(Continued)

(52) U.S. Cl.
CPC ............... *A61B 3/14* (2013.01); *A61B 3/06* (2013.01); *A61H 31/005* (2013.01);
(Continued)

(58) Field of Classification Search
CPC ........... A61B 3/14; A61B 3/0025; A61B 3/06; G16H 20/40; G16H 50/20; A61H 31/00;
(Continued)

(56) References Cited

U.S. PATENT DOCUMENTS 8,880,166 B2 11/2014 Tan et al.
2008/0255482 A1* 10/2008 Lurie .................... A61H 31/00
601/43
(Continued)

FOREIGN PATENT DOCUMENTS

GB 1286016 8/1972
WO 2015/042413 3/2015
WO WO-2015042413 A1 * 3/2015 ............. A61B 3/112

OTHER PUBLICATIONS

International Search Report and Written Opinion dated May 27, 2016 in international application No. PCT/US2016/021353, 23 pages.

Primary Examiner — James R Greece
(74) Attorney, Agent, or Firm — Fish & Richardson P.C.

(57) ABSTRACT

In an example implementation, a system includes one or more memory devices configured to store computer readable instructions, and a treatment adjustment engine that includes one or more processing devices. The treatment adjustment engine is configured to obtain a first image of an eye of a subject, and a second image of the eye of the subject. The second image is captured in the presence of an electronic light source. The treatment adjustment engine is further configured to determine, based on the first and second images, one or more metrics representing shapes of the iris and pupil in the corresponding images, and determine, based on the one or more metrics, a pupillometry measure of the subject. The treatment adjustment engine is also configured to generate a signal for adjusting a cardiopulmonary therapy based on the determined pupillometry measure.

24 Claims, 7 Drawing Sheets

(51) Int. Cl.
*A61B 3/06* (2006.01)
*G16H 50/20* (2018.01)
*G16H 20/40* (2018.01)

(52) U.S. Cl.
CPC .......... *A61H 31/006* (2013.01); *G16H 20/40* (2018.01); *G16H 50/20* (2018.01); *A61H 2201/0188* (2013.01); *A61H 2201/1604* (2013.01); *A61H 2201/5005* (2013.01); *A61H 2201/5012* (2013.01); *A61H 2201/5048* (2013.01); *A61H 2230/085* (2013.01)

(58) Field of Classification Search
CPC .... A61H 31/005; A61H 31/006; G06F 19/00; G06F 19/3481
USPC ................................ 351/200, 205–206, 246
See application file for complete search history.

(56) References Cited

U.S. PATENT DOCUMENTS

2011/0149239 A1* 6/2011 Neal .................... A61B 3/0025
351/205
2012/0134471 A1 5/2012 Krautim et al.
2013/0088685 A1* 4/2013 Holland ............. G06K 9/00604
351/206

\* cited by examiner

US 10,561,316 B2

PUPILLOMETRY BASED CARDIOPULMONARY THERAPY

CROSS-REFERENCE TO RELATED APPLICATION

This application is a U.S. National Phase Application under 35 U.S.C. § 371 of International Patent Application No. PCT/US2016/021353, filed on Mar. 8, 2016, which claims the benefit of U.S. Provisional Application No. 62/139,460, filed Mar. 27, 2015.

TECHNICAL FIELD

The technology described in this document is directed to non-invasive feedback techniques in emergency injury management.

BACKGROUND

A goal of intensive care management of traumatic brain injury (TBI) is to prevent and treat secondary ischemic injury. This can be done using a neuro-protective strategy that maintains cerebral perfusion to meet the brain's metabolic demands for oxygen and glucose. Because the skull is substantially non-expandable, an increase in intracranial pressure (ICP) may impede cerebral blood flow (CBF) and lead to cerebral ischemia. Increased ICP is an important cause of secondary brain injury. Therefore, prevention and control of increased ICP and maintenance of cerebral perfusion pressure (CPP) are important therapeutic goals in managing and treating TBI. ICP monitoring can be an invasive process and may not be immediately available when TBI occurs and/or is diagnosed (e.g., at an emergency scene).

SUMMARY

In one aspect, this document features a system that includes one or more memory devices configured to store computer readable instructions, and a treatment adjustment engine that includes one or more processing devices. The treatment adjustment engine is configured to obtain a first image of an eye of a subject, and a second image of the eye of the subject. The second image is captured in the presence of an electronic light source. The treatment adjustment engine is further configured to determine, based on the first and second images, one or more metrics representing shapes of the iris and pupil in the corresponding images, and determine, based on the one or more metrics, a pupillometry measure of the subject. The treatment adjustment engine is also configured to generate a signal for adjusting a cardiopulmonary therapy based on the determined pupillometry measure.

In another aspect, this document features a method that includes obtaining a first image of an eye of a subject, and obtaining a second image of the eye of the subject. The second image is captured in the presence of an electronic light source. The method also includes determining, based on the first and second images, one or more metrics representing the shapes of the iris and pupil in the corresponding images, and determining, based on the one or more metrics, a pupillometry measure of the subject. The method further includes generating a signal for adjusting a cardiopulmonary therapy based on the determined pupillometry measure.

In another aspect, the document features one or more machine-readable storage devices having encoded thereon computer readable instructions that cause one or more processors to perform various operations. The operations include obtaining a first image of an eye of a subject, and obtaining a second image of the eye of the subject. The second image is captured in the presence of an electronic light source. The operations also include determining, based on the first and second images, one or more metrics representing the shapes of the iris and pupil in the corresponding images, and determining, based on the one or more metrics, a pupillometry measure of the subject. The operations further include generating a signal for adjusting a cardiopulmonary therapy based on the determined pupillometry measure.

Implementations of the above aspects can include one or more of the following features.

The cardiopulmonary therapy can include a pressure associated with intrathoracic pressure regulation (IPR). The signal for adjusting the IPR pressure can represent a pressure decrease that is held until reflected in the pupillometry measure. The pressure decrease can be provided in a series of 1 mm Hg increments. The pressure decrease can be held between approximately ten seconds and two minutes. The treatment adjustment engine can be operated in a repetitive manner to dynamically adjust the IPR pressure based on pupillometry measures determined over a period of time. The pupillometry measure can be determined at least every ten seconds to dynamically adjust the IPR pressure.

Obtaining the first image can include presenting, on a display device, user interface that includes a graphical element for specifying boundaries for the first image, and generating a control signal for an imaging device to capture the first image based on a user-input received via the user interface. Obtaining the second image can include presenting, on a display device, a user interface that includes a graphical element for specifying an area of the eye to be included in the second image, generating a first control signal for activating the electronic light source, and generating a second control signal for an imaging device to capture the second image based on a user-input received via the user interface.

Determining the one or more metrics can include determining a first metric as a function of (i) iris area and (ii) pupil area as captured in the first image, and determining a second metric as a function of (i) iris area and (ii) pupil area as captured in the second image. The pupillometry measure can be determined based on the first metric and the second metric. The cardiopulmonary therapy can include at least one of ventilation or chest compression. The signal for adjusting the cardiopulmonary therapy can include a feedback signal. The feedback signal can cause an adjustment in a device delivering at least a portion of the cardiopulmonary therapy. The signal for adjusting the cardiopulmonary therapy can include an audible or visual signal representing a feedback related to the cardiopulmonary therapy.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

The adult brain is enclosed in a rigid skull, and for intracranial pressure (ICP) to remain substantially constant, the volume enclosed within the skull must not vary significantly. The ICP has two primary components: (i) the pressure due to cerebrospinal fluid (CSF) and (ii) the vasogenic pressure. The CSF pressure regulates the baseline ICP. In certain pathologic states, the CSF pressure may increase, causing an increase in ICP. For example, the CSF pressure may increase because of resistance to CSF flow between intracerebral compartments secondary to brain swelling or expansion of intracranial mass lesions, or because of CSF outflow being obstructed. The vasogenic component of the ICP can cause small fluctuations of cerebral blood volume (CBV) thereby contributing to corresponding fluctuations in the overall ICP. For example, an increase in the vasogenic pressure may be caused by hypercapnea, increase in cerebral metabolism, and/or cerebral hyperemia.

In order to maintain a substantially constant ICP, any volume increase in the intracranial cavity (e.g., due to the swelling of a portion of the brain) may require a compensatory reduction in pressure due to one of the ICP components. Because brain tissue is essentially incompressible, any increase in overall ICP due to such brain swelling initially results in extrusion of CSF and (mainly venous) blood from the intracranial cavity. This is often referred to as "spatial compensation." During spatial compensation, CSF can be expelled from the intracranial cavity into a reservoir located in the spinal theca.

Figure 1:
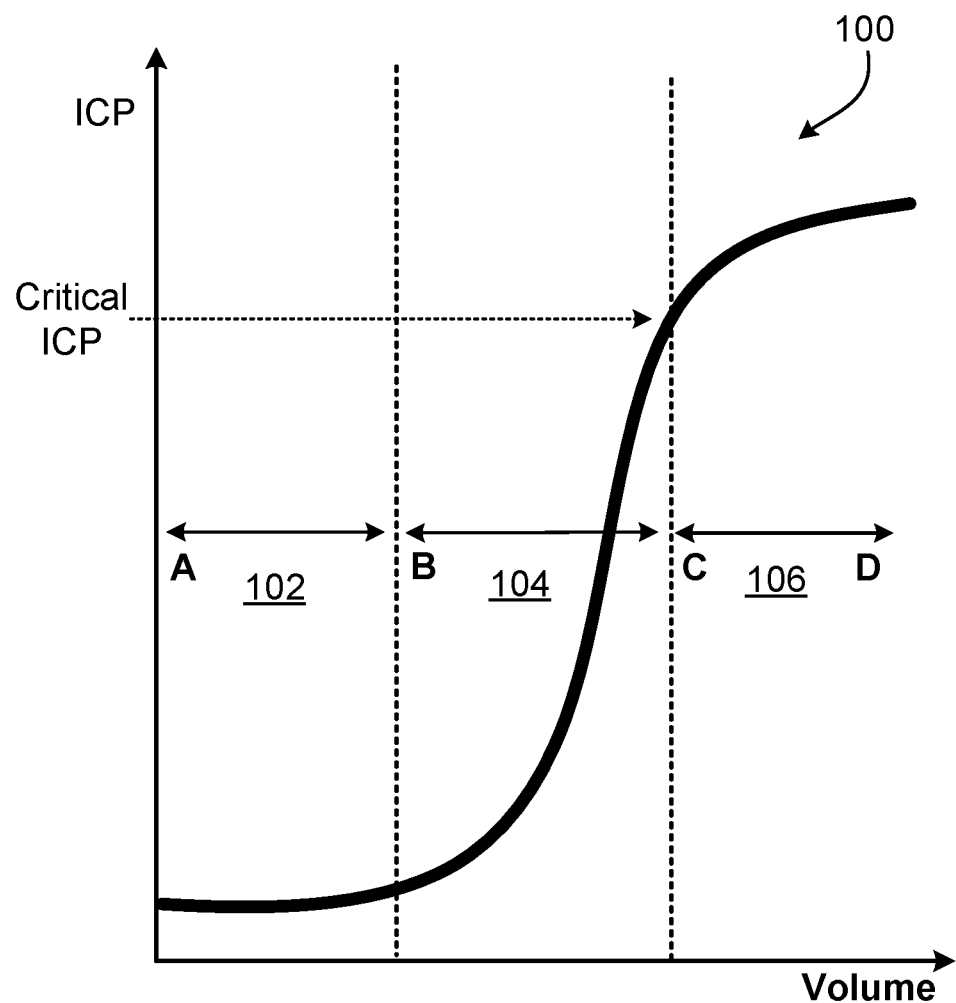
FIG. 1 is a chart that depicts a relationship between brain volume and intracranial pressure.

FIG. 1 illustrates a relationship between ICP and intracranial volume via a pressure-volume curve 100 that comprises of three parts. This curve is based on data presented in the publication: *Monitoring intracranial pressure in traumatic brain injury*, by M. Smith, *Anesth. Analg.* 2008; 106:240-8. As represented by the region 102 of the curve, because compensatory reserves are adequate, the ICP remains substantially constant in this region low despite increases in intracerebral volume. Once such compensatory mechanisms are exhausted, the pressure-volume curve increases in an exponential fashion. This is represented by the region 104 in FIG. 1. In the region 104 the intracranial compliance is significantly reduced, and a small increase in intracerebral volume therefore causes a substantial increase in ICP. At even higher volume levels, the rate of increase of the ICP plateaus as the capacity of cerebral arterioles to dilate in response to a reduction in cerebral perfusion pressure (CPP) is substantially exhausted. This is represented by the region 106 of FIG. 1. The region 106 represents a situation where the high brain tissue pressure may result in collapse of dysfunctional vessels as cerebrovascular responses become terminally or non-reversibly disrupted.

Elevated levels of ICP can be treated using one or more techniques, such as aggressive fluid resuscitation to maintain the mean arterial blood pressure greater than a threshold level (e.g., 90 mmHg in some individuals), control of oxygen and carbon dioxide partial pressures through mechanical ventilation, mild-moderate hyperventilation, sedation, lowering the body temperature, prevention of jugular venous outflow obstruction by head elevation, pharmacological therapy including hyperosmolar agents (e.g., mannitol and hypertonic saline) and anesthetics, CSF drainage, decompressive craniotomy, etc. In some cases, treatments can be applied in a step-wise fashion until the ICP is reduced to a desirable level. In the absence of intervention, elevated ICP and decreased cerebral perfusion may lead to morbidity and mortality for patients with brain injury.

Various cardiopulmonary therapy techniques may be used in treating brain injuries. In some cases, Intrathoracic Pressure Regulation (IPR) can be used in treating brain injuries. IPR can be administered, for example, using a device that is inserted into a standard respiratory circuit between the patient and a mechanism for providing positive pressure ventilation. The setup can be configured such that after a positive pressure ventilation, the IPR lowers intrathoracic pressure to subatmospheric levels relative to the rest of the body. This can enhance blood return to the heart, decrease ICP, and improve cerebral perfusion pressure (CPP).

The decrease in ICP achieved via IPR may have undesirable side-effects. For example, in one particular study, IPR was delivered using a ventilation adjunct device (CirQlator®, manufactured by Advanced Circulatory Systems, Inc. of Roseville, Minn.) that generates −12 cm $H_2O$ airway pressures during the expiratory phase of ventilation. See Shock, Publish Ahead of Print, DOI:10.1097/SHK.0000000000000314. The study showed that while the IPR was found to significantly improve coronary perfusion pressure as well as coronary blood flow, in some cases, the negative pressure reduced oxygenation, which was manifested in reduced $O_2$ saturation levels and arterial oxygenation ($PaO_2$). Id. Therefore, administering IPR may require various types of monitoring, including, for example, multimodal brain monitoring such as continuous brain-tissue oxygenation, near infrared spectroscopy, transcranial Doppler ultrasonography, microdialysis, etc. However, equipment required for such monitoring may not be available at sites of emergencies (e.g., an accident scene) where brain injuries occur and/or are diagnosed. In some instances such monitoring may require drilling holes in the skull for intracranial pressure measurements, invasive arterial pressure lines, etc., which may not be available at typical pre-hospital or emergency scenes where a person is initially being treated for cerebral hypertension resulting from TBI.

This document describes treatments that employ portable, non-invasive, and pupillometry-based technology that can be used by personnel such as first responders to determine or titrate the amount of negative pressure associated with IPR. For example, the technology can be used to titrate the negative pressure (e.g., as administered using the CirQlator® device) such that the administered negative pressure keeps the intracranial pressure of the patient in the region of good compensatory reserve (e.g., as represented in FIG. 1 as region 102, and possibly as portion of the region 104 where the rate of increase of ICP is below a threshold), without exacerbating negative effects due to reduced oxygenation.

Figure 2:
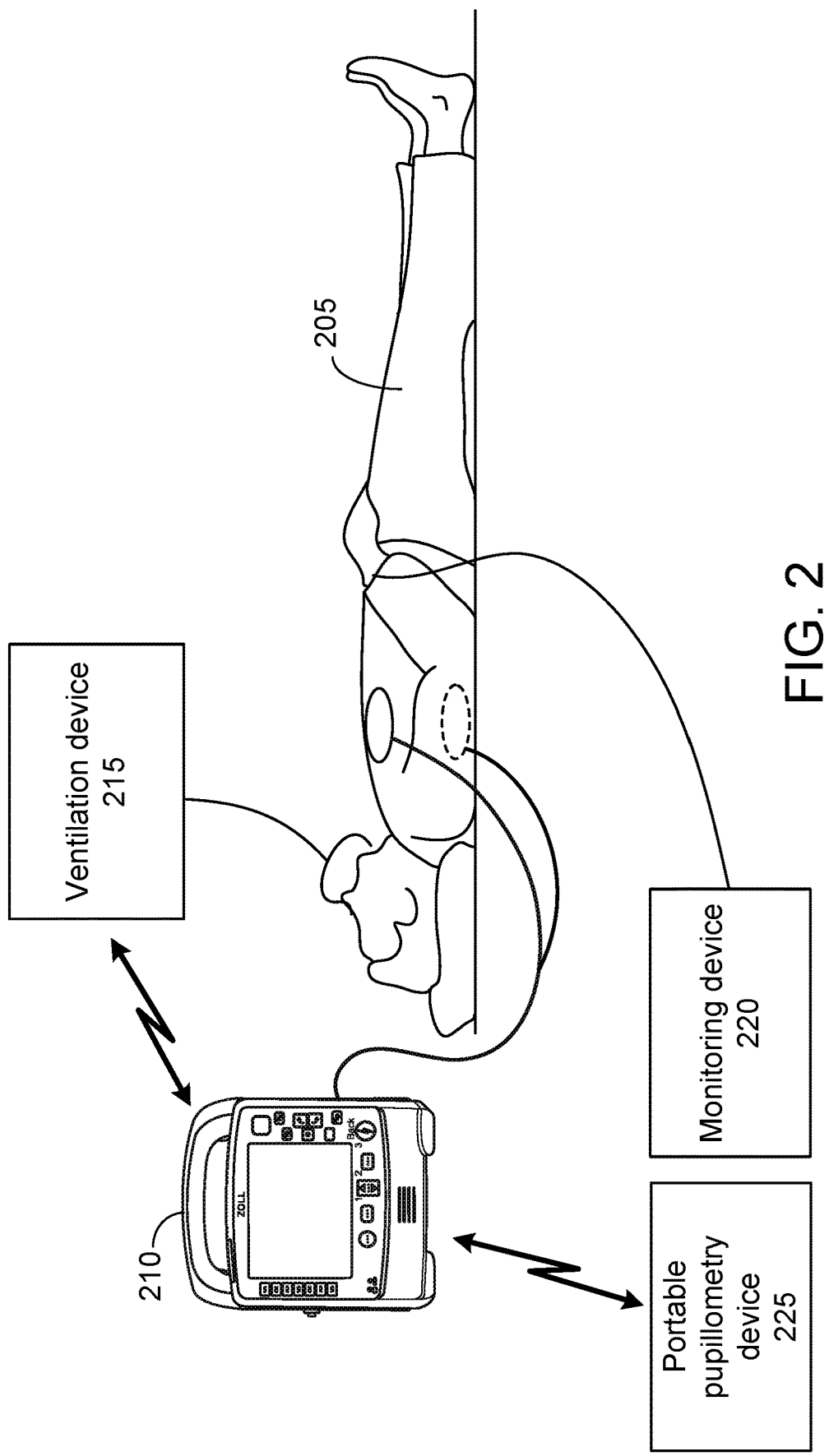
FIG. 2 depicts an example of an emergency situation where the technology described herein may be used.

FIG. 2 depicts an example of an emergency scene where the technology described herein may be used. In such an emergency situation, a patient (also referred to as a subject or victim) 205 may be treated and/or monitored using various portable or ambulatory therapeutic and/or monitoring devices. Examples of such devices can include, for example, a defibrillator 210 (e.g., Propaq automated external defibrillator (AED) manufactured by ZOLL Medical of Chelmsford, Mass.), and/or a ventilator (or ventilator adjunct) device 215 (e.g., CirQlator® IPR device manufactured by Advanced Circulatory Systems, Inc. of Roseville, Minn.). The medical devices can also include a separate monitoring device 220 configured to monitor various physiological parameters associated with the patient 205. In some cases, one or more of the devices 210, 215, and 220 can be integrated into one physical unit or a combination of unites. One or more of the medical devices 210, 215, and 220 can be configured to communicate with one another over wired, wireless, etc. connections (e.g., Wi-Fi, Bluetooth® etc.).

In some implementations, one or more auxiliary monitoring devices can be used for providing feedback on therapy administered using one or more therapeutic devices (e.g., the devices 210, 215, etc.). Such auxiliary devices can be configured to execute one or more diagnostic assessments such as pupillometry (to measure pupillary response), neural assessment (e.g., via a Glasgow Coma Score), pulse oximetry, etc. An example of such an auxiliary device includes a portable pupillometry device 225 such as an infrared pupillometer (e.g., the ForSite® pupillometer manufactured by NeurOptics Inc., Irvine Calif.). In some implementations, a mobile device such as a smartphone, tablet, or other type of computing device can be used to implement functions of the portable pupillometry device 225. In some implementations, the portable pupillometry device 225 can include a treatment adjustment engine that can communicate with one or more therapeutic devices (e.g., the devices 210 or 215) to provide a control signal based on the results of pupillometry on the patient 205. For example, the portable pupillometry device 225 can be connected via a wired or wireless connection to the ventilator device 215 to provide control signals that cause adjustments to the level of IPR administered by the ventilation device 215.

In some arrangements, the ventilator device 215 can be configured to adjust pressure level based on a control signal (also referred to as a feedback signal) from the portable pupillometry device 225. For example, the negative pressure—which may be initially set at a preset value (e.g., −12 mmHg)—can be dynamically adjusted based on the control signals generated by the portable pupillometry device 225 based on pupillometric measurements. In some implementations, the ventilator device 215 cycles through preset values within a range (e.g., between zero and −25 mm Hg) based on feedback received from the portable pupillometry device 225.

To assist with operations, the ventilator device 215 can be configured to search for a portable pupillometry device 225, and initiate communication with the device 225 if one is found. In some implementations, the communication between the portable pupillometry device 225 and the ventilator device 215 is automatically initiated at the portable pupillometry device 225. Once a connection is established between the portable pupillometry device 225 and the ventilator device 215, an IPR therapy titration cycle can be initiated. Such initiation can be based on, for example, user input received either at the portable pupillometry device 225, or the ventilator device 215. For example, the user input can be provided using a control such as a button, touch screen icon displayed on a display device or monitor associated with either device, etc. The display device can also be configured to provide user instructions on how to use the portable pupillometry device 225. The instructions can also be provided via another output device such as one or more speakers. Once the portable pupillometry device 225 is positioned for performing pupillometry, the pupillometry device can execute a process for measuring pupil reflex and accordingly generate a control signal for a connected therapeutic device (the ventilator device 215, in this example).

In some implementations, based on the feedback from the portable pupillometry device 225, the ventilator device 215 decreases the pressure, for instance, in steps of approximately 1 mm Hg increments, and holds a particular pressure for a clinically relevant period of time to allow the pressure change to have an effect on the pupil response. The clinically relevant period can range, for example, from 10 seconds to 2 minutes. The pupil response measurement can be taken, for example, at intervals of ten seconds or longer, so as not to develop accommodation to light stimulus used during the measurements (something that may affect the accuracy of the measurements). The ventilator device 215 can be configured to record both when and how large was the pressure change as well as the instantaneous pupillometric measurements. For each pressure setting during the titration cycle, at least one pupillometric measurement can be made.

Information about the patient's health parameters can be obtained from the pupillometric measurements made during the titration cycle. For example, if the patient has compromised coronary perfusion, a sigmoidal response in pupillometric measurements such as constriction velocity may be reflected in a graph representing constriction velocity vs. IPR pressure. Such a graph may show the constriction velocity to be depressed for lower magnitude negative pressures and with a knee somewhere in the range of 0 and −25 mm Hg. In some cases, above a threshold, the changes in pupillometric measurements for a given change in IPR pressure may be insignificant. The set point for the IPR pressure can therefore be chosen with respect to the flattened region of the curve, for example, 10-20% below (more negative) the knee of the curve for margin.

Various pupillometric measurements can be performed by the portable pupillometry device 225. Examples of such pupillometric measurements include constriction velocity, maximum and minimum apertures, dilation velocity, apertures and/or percentage of change. In one study of healthy volunteers, the following pupil measures were found: mean maximum resting aperture was 4.1±0.34 mm, whereas the mean minimum aperture after stimulation was 2.7 mm. The mean constriction velocity in their study was 1.48±0.33 mm/second. The latency period varied from 120 to 360 mm/second. The mean percentage of reduction in pupil size after stimulation was 34%. See *Clinical Implications of Quantitative Infrared Pupillometry in Neurosurgical Patients*, Neurocrit. Care 2006; 05:55-60.

Since more than one measure of a particular pupil parameter such as constriction velocity may be taken during the time an IPR pressure is held fixed during the titration cycle, the transient response of the intracranial cerebrovascular system can be estimated. In some implementations, the change in pupil parameter may be estimated as an exponential response, and the magnitude and time constant for the response can be calculated to estimate the degree of pupil change for each quantum of change in IPR pressure. In some implementations, instead of the above described linear process, the individual pressure settings can be varies based on a search process, e.g., binary search or random sequence search. This can be done, for example, to reduce the amount of time required for titration of therapy.

In some implementations, the initial pressure value for the titration cycle may be set to a maximal (e.g., most negative) value such as −12 mm Hg. The negative pressure can then be gradually lessened (i.e., made less negative) until a particular pupil parameter begins to degrade. For instance, if the constriction velocity decreases below 0.8 mm/sec during the titration cycle, the IPR pressure value can be chosen to be a more negative value such that the velocity is above 1.0 mm/sec. In some cases, the initial IPR pressure for the titration cycle can be chosen to be zero, and then made more negative. In such cases, a titration threshold can be chosen as corresponding to the constriction velocity increasing above a value in the range of 0.8-1.24 mm/sec. The titration threshold can also be chosen as corresponding to the constriction velocity increasing by more than 0.2 mm/sec.

During runtime operations of administering IPR therapy, small changes to IPR can be made at regular intervals (e.g., every 10 minutes) with the aim of converging to the titration point. For example, magnitude of the negative pressure can be adjusted as needed to move away the region 106 depicted in FIG. 1.

While the description above uses constriction velocity to describe the pupillometric feedback based IPR adjustment, other pupillometric measurements can also be used. For example, pupillometric measurements may be taken from both eyes at the same time, for example, using dual pupillometers. In some implementations, pupil asymmetry (aniscoria) may also be used because aniscoria in excess of 0.5 mm Hg has been shown to have association with cerebral hypertension.

Figure 3A:
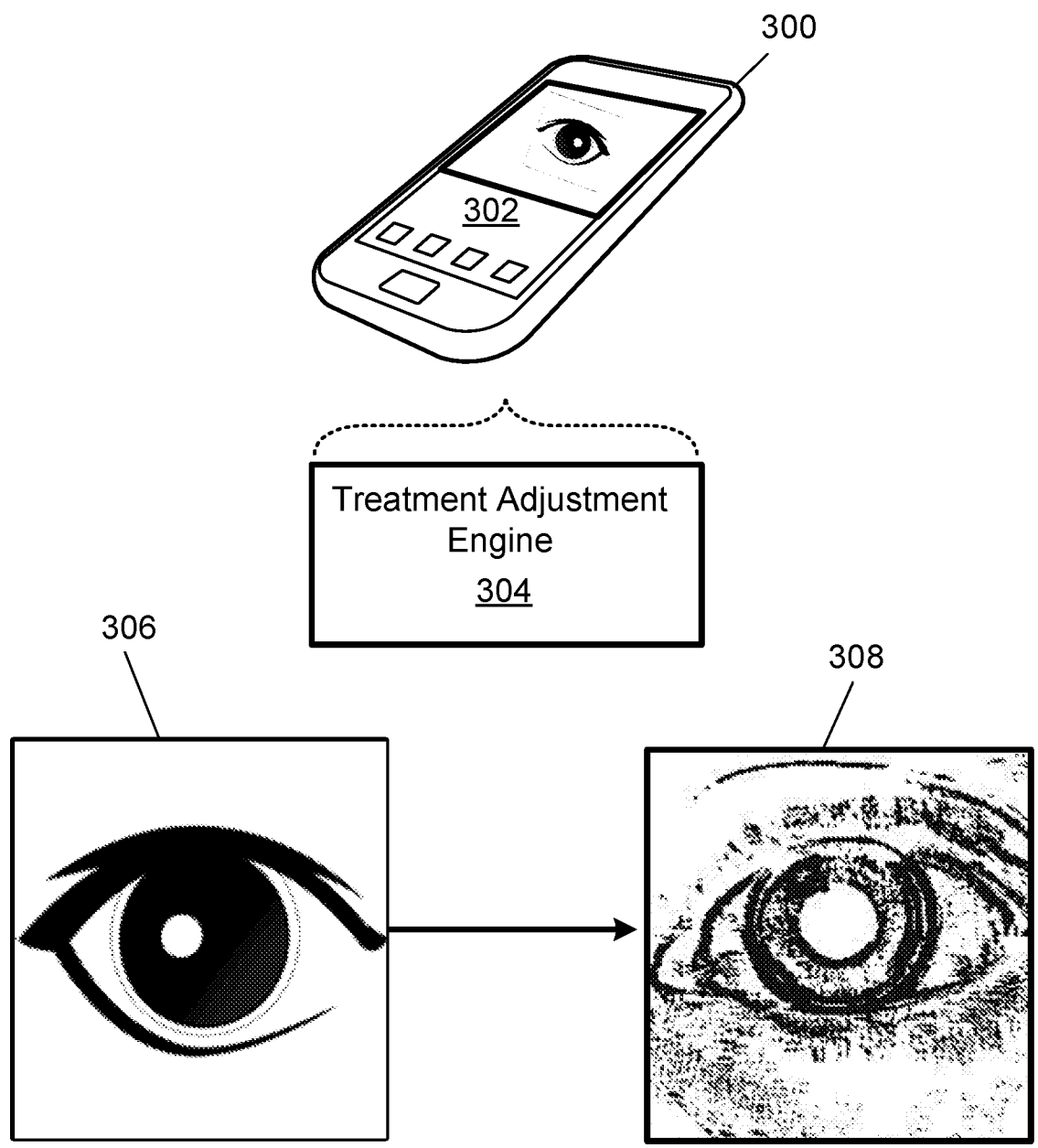
FIG. 3A illustrates an example of pupillometry using a mobile device.

In some implementations, functions of the portable pupillometry device 225 can be implemented on a mobile device 300 as shown in FIG. 3A. This allows for potentially low cost implementations that leverage processing power and hardware (e.g., camera, processing devices, display etc.) available on a mobile device to achieve the functionalities of a portable pupillometry device 225. This also allows for personnel such as first responders to use their mobile devices to obtain and use pupillometric measurements as described above with reference to FIG. 1. In such implementations, the mobile device 300 can execute a treatment adjustment engine 304 that obtains one or more images of the patient's eye(s) (for example, using a camera of the device), determines one or pupillometric measures from the obtained images, and generates, based on the pupillometric measures, a signal (e.g., a control signal or feedback signal) that causes an adjustment of IPR pressure administered by a therapeutic device.

In some implementations, the treatment adjustment engine 304 can be launched, for example, by an application executing on the mobile device. Such an application can be made available to a user of the mobile device 300 as a third-party application downloadable from an electronic marketplace of third party applications. In some implementations, the treatment adjustment engine 304 can be configured to present, on a display 302 of the mobile device, a user interface that allows the user to initiate the functionalities of the portable pupillometry device 225. For example, the treatment adjustment engine 304 can initiate, possibly based on an initial user-input, an automated process that obtains one or more images of the patient's eyes and calculates a pupillometric measure from the images. The user input can include, for example, holding the mobile device 300 proximate to the user such that an open eye of the user is within the range of the viewfinder of the camera of the mobile device 300. In some implementations, the treatment adjustment engine 304 can access the camera of the mobile device 300 and present a graphical element for specifying the boundaries of the images(s). Once the user positions the mobile device 300 such that the patient's open eye is viewable on the display 302 within graphical element, the treatment adjustment engine 304 can be configured to initiate the automated pupillometric measurement process.

The automated process can include, for example, capturing one or more images 306 of the eye of the patient. The images 306 can include images obtained both in the presence and absence of artificial illumination. For example, the treatment adjustment engine 304 can first obtain one or more first images in the absence of any artificial illumination, and then access the flash of the mobile device 300 (or another electronic light source configured to direct light towards the open eye of the patient) to cause the flash (or another electronic light source) to be turned on. The treatment adjustment engine 304 can be configured to obtain one or more second images when the flash or another electronic light source is illuminating the patient's eye. The first and second images (obtained in the absence and presence, respectively, of illumination from the electronic light source) can then be compared to generate a pupillometric measurement.

Generating the pupillometric measurement can include executing one or more image processing techniques on the captured images. In some implementations, this includes executing processes to locate and determine the size of the pupil and/or the iris in images captured both in the presence and the absence of flash. Such processes can include high-pass filtering to produce a high-frequency version 308 of the obtained images. An edge detection process can be executed to locate the position of the pupil and the iris. Because a normal pupil is supposed to constrict in the presence of artificial illumination being directed towards the pupil, pupillary reflex can be determined, for example, from the ratio of the pupil area to the image area in images taken both in the presence and absence of artificial illumination. For example, if the ratio of the pupil area to the image area in the presence of artificial light is unchanged from the corresponding ratio in the absence of light, this would indicate an absence of pupillary reflex. Conversely, a significant change in the ratios would indicate a high degree of pupillary reflex. In some implementations, the amount of change between the ratios may be used to determine a degree of pupillary reflex.

Figure 3B:
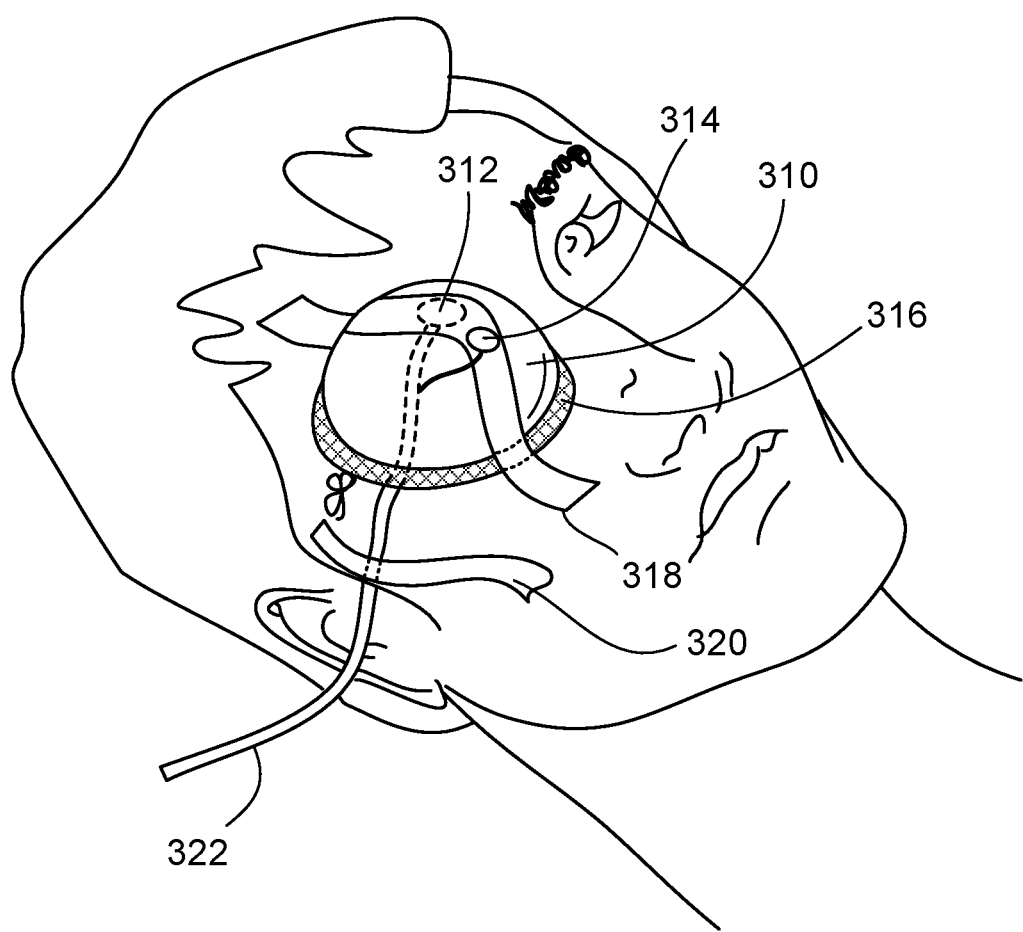
FIG. 3B illustrates an example of a portable pupillometer.

In some implementations, the portable pupillometry device 225 can include an eyecup 310 as shown in FIG. 3B. In some implementations, such an eyecup 310 can include a camera 312 and an electronic light source 314. The eyecup 310 can be flexible, and conformable to face contours. Various constructions techniques may be employed, for example, the eyecup 310 may be molded from a urethane or other flexible medical grade, biocompatible polymer. The durometric value of the cup material and shape of the cup lip may be chosen to produce a lip 316 which can be squeezed together with a force of less than 1 pound. The durometric value is a measure of the hardness or stiffness of a material, such as an elastomer, as measured using a durometer. During placement on the patient's eye, the cup lips 316 are squeezed together slightly, then placed lightly with the rim superior and inferior to the eye ball on the skin of the closed eye. As the cup lips 316 are released, while pressure is maintained on the eye, the eyelids are opened. A piece of affixation tape 318 can then be applied to hold the cup 310 in place.

The camera 312 can include various parts. In some implementations, the camera 312 includes, for example, an OV4682 4-megapixel infrared sensitive chip, with HD capabilities up to 120 frames per second (manufactured by Omnivison of Santa Clara, Calif.). In some implementations, the camera 312 can include a lens such as liquid lens such as manufactured by Varioptic of France. The electronic light source 314 can include, for example, white light and infrared LEDs. In some cases, a small length of strain relief tape 320 may be employed to prevent cable-induced motion from degrading the camera images. Interface electronics may be incorporated into the cable assembly 322 directly to control the camera 312 and light sources 314. The cable assembly 322 can also be configured to bi-directionally communicate with one or more devices (e.g., the ventilator 215) via a USB interface that may be used for both power and communication. The cup 310 can also include circuitry for communicating wirelessly with one or more devices.

Returning to FIG. 2, the defibrillator device 210 can be used, for example, to monitor and/or treat conditions associated with the heart of the patient 205. In general, the heart relies on an organized sequence of electrical impulses to beat effectively. Deviations from this normal sequence are known as "arrhythmia." In some implementations, the defibrillator 210 can be configured to execute signal processing processes that analyze electrocardiography (ECG) signals acquired from the patient 205 to determine the presence or absence of cardiac arrhythmia such as ventricular fibrillation (VF) or shockable ventricular tachycardia (VT). In some implementations, the device 210 can include, or work in communication with devices such as ECG rhythm classifiers, and ventricular arrhythmia detectors. The device 210 can be configured to deliver controlled electrical shock to a patient to administer therapy for the heart of the patient. In some implementations, the device 210 can be configured to detect and/or differentiate between different cardiac waveforms such as VT and VF.

In some implementations, the device 210 can be configured to treat VT. VT is a tachydysrhythmia that originates from a ventricular ectopic focus, characterized by a rate that is typically greater than 120 beats per minute and wide QRS complexes. VT may be monomorphic (typically regular rhythm originating from a single focus with identical QRS complexes) or polymorphic (unstable, may be irregular rhythm, with varying QRS complexes). Depending on the rate and the length of time that the VT has been sustained, a heart in the VT state may or may not produce a pulse (i.e., pulsatile movement of blood through the circulatory system). If there is no pulse associated with this VT rhythm, then the VT is considered to be unstable and a life threatening condition. In some implementations, the device 210 can be configured to treat an unstable VT with an electrical shock or defibrillation.

The defibrillator device 210 can also be configured to treat supraventricular tachycardia (SVT). SVT is a rapid heartbeat that begins above the heart's lower chambers (the ventricles). SVT is an abnormally fast heart rhythm that begins in one of the upper chambers of the heart (atria), a component of the heart's electrical conduction system called the atrioventricular (AV) node, or both. Although SVT is rarely life-threatening, its symptoms, which include a feeling of a racing heart, fluttering or pounding in the chest or extra heartbeats (palpitations), or dizziness can be uncomfortable.

In some implementations, the defibrillator device 210 can be configured to detect and/or treat VF, which is usually an immediate threat to life. VF is a pulseless arrhythmia with irregular and chaotic electrical activity and ventricular contraction in which the heart immediately loses its ability to function as a pump. VF is the primary cause of sudden cardiac death (SCD). Usually, VF activity is highly unlikely to pump any blood. Therefore, upon detection of VF, the device 210 can be configured to defibrillate the heart using an electrical charge.

In some implementations, the device 210 can be configured to recognize the VT and VF waveforms by performing ECG analyses at specific times during a rescue event of a patient using defibrillation and cardio-pulmonary resuscitation (CPR). In some implementations, the device 210 can include motion sensors such as accelerometers to measure the rescuer's performance of CPR and provide feedback to the rescuer in the form of audio-visual prompts.

Figure 4:
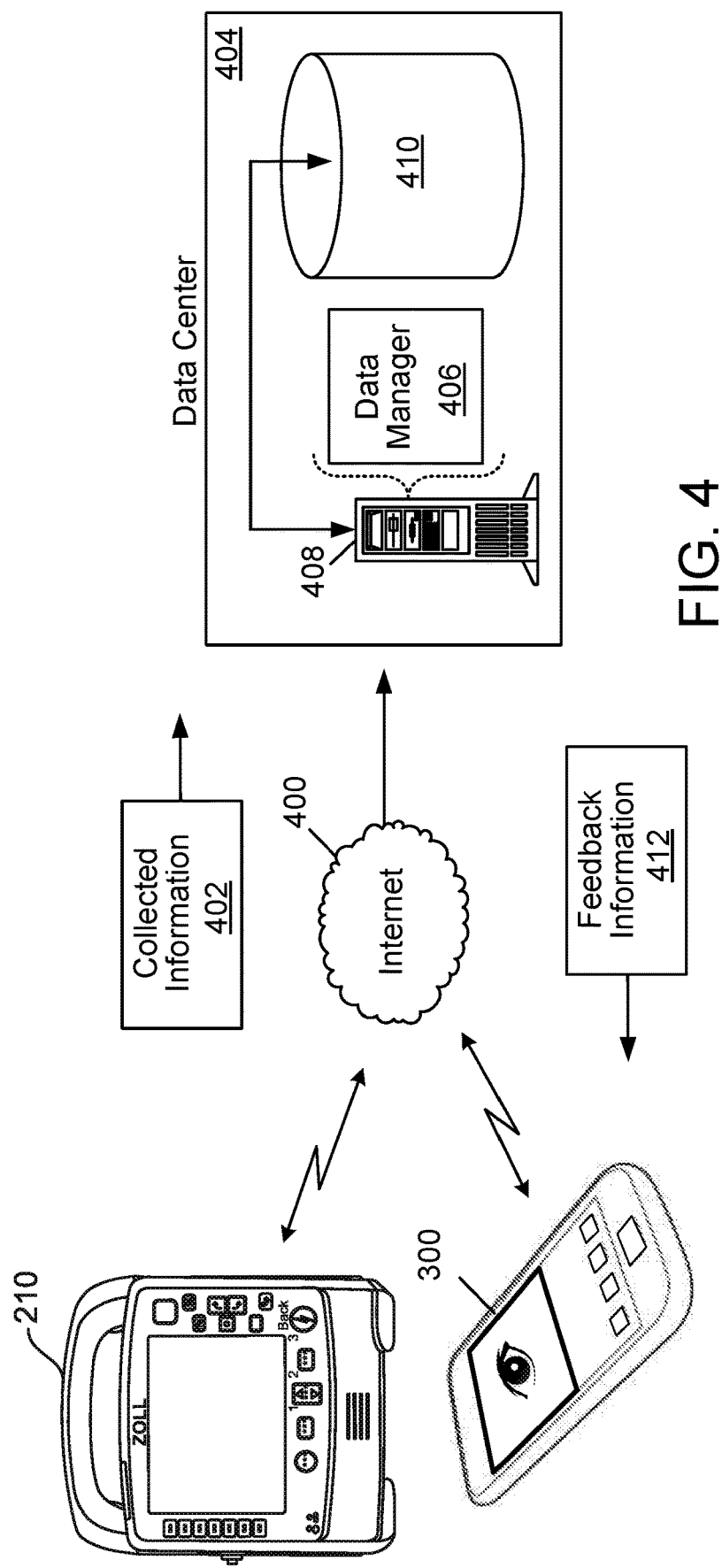
FIG. 4 shows an example of an environment in which the technology described herein can be implemented.

Referring to FIG. 4, various types of computing architectures may be employed for exchanging information from the emergency scene to other locations (e.g., a hospital, emergency response vehicle, first responders on route, etc.). In the relatively simply illustration, information can be sent from the received by the defibrillator 210, the smart phone 300, etc. via one or more network (e.g., the Internet 400). For example, information collected 402 by these devices may be sent to a data center 404 (e.g., located at a hospital) for processing (e.g., further analysis such as comparative studies), storage, etc. In this example, a data manager 406 is executed by a server 408 located at the data center 404. The collected information 402 can be stored at the data center (e.g., on a storage device 410 located that the center), at other locations (e.g., external from the data center 404), etc. From the various processed executed by the server 408 (e.g., via the data manager 406, applications, etc.) information may be attained that can assist the treatment of patients at the emergency or future scenes. For example, parameters associate with collecting pupil imagery (e.g., frequency of image capture, time of image capture, etc.) may be determined at the data center 404 and relayed to the devices used by the rescuers (e.g., defibrillator 210, the smart phone 300, etc.). In this illustration, feedback information 412 is sent from the data center 404 via the Internet 400 to one or more of the devices. Along with assisting with information collection (e.g., provide image capture parameters), data can be provided for assisting with other rescue aspects (e.g., update instructions, data, etc. to assist with processing the captured pupil imagery at the emergency scene).

Figure 5:
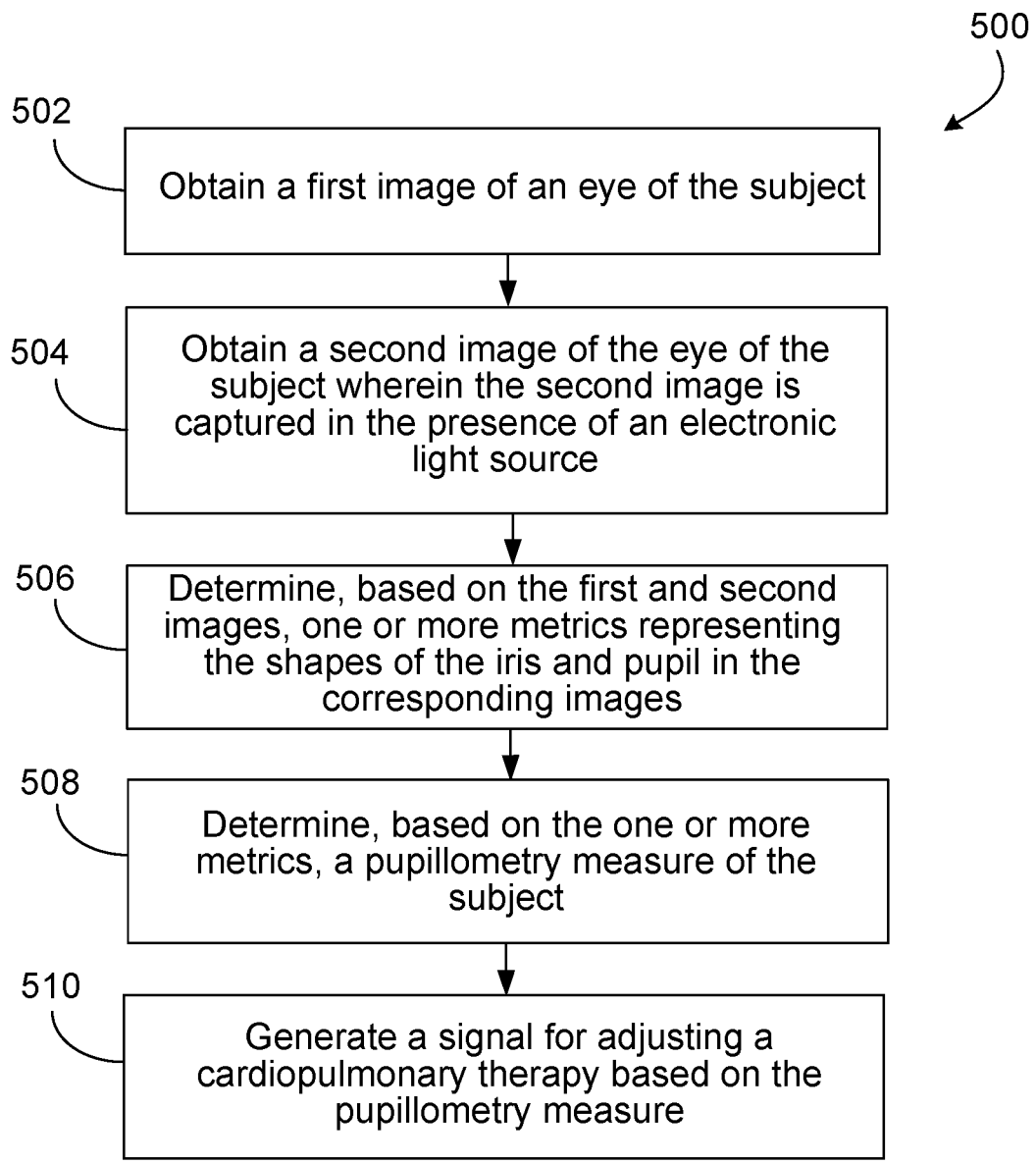
FIG. 5 is a flowchart of an example process for adjusting cardiopulmonary therapy based on pupillometry.

FIG. 5 is a flowchart of an example process 500 for adjusting a cardiopulmonary therapy based on pupillometry. The operations of the process 500 can be performed, at least in part, in the treatment adjustment engine of a portable pupillometry device 225 described above with reference to FIG. 2. In some implementations, at least some of the operations of the process 500 can be executed at a remote computing device such as the server 408 described with reference to FIG. 4.

Operations of the process 500 includes obtaining a first image of an eye of the subject (502). In some implementations, the first image can be an image obtained by a camera such as one disposed in a mobile device (e.g., smartphone or tablet). In some implementations, the first image can be an infrared image as obtained, for example, an infrared pupillometer. Is some implementations, obtaining the first image can include presenting, on a display device, user interface that includes a graphical element for specifying boundaries for the first image, and generating a control signal for an imaging device to capture the first image based on a user-input received via the user interface.

Operations of the process 500 also includes obtaining a second image of the eye of the subject, wherein the second image is captured in the presence of an electronic light source (504). In some implementations, the electronic light source is automatically activated prior to obtaining the second image. The electronic light source can include, for example, a flash disposed in a mobile device or an external light source that can be controlled by the mobile device (or the portable pupillometry device). In some implementations, obtaining the second image comprises presenting, on a display device, a user interface that includes a graphical element for specifying an area of the eye to be included in the second image, generating a first control signal for activating the electronic light source, and generating a second control signal for an imaging device to capture the second image based on a user-input received via the user interface.

The operations of the process 500 also includes determining based on the first and second images, one or more metrics representing the shapes of the iris and pupil in the corresponding images (506). The one or more metrics can include, for example, a first metric as a function of (i) iris area and (ii) pupil area as captured in the first image, and a second metric as a function of (i) iris area and (ii) pupil area as captured in the second image. The first metric can be a ratio of the pupil area to the iris area as captured in the first image. The second metric can be a ratio of the pupil area to the iris area as captured in the second image.

The operations of the process 500 further includes determining, based on the one or more metrics, a pupillometry measure associated with the subject (508). In some implementations, the pupillometry measure can include any of the measures described above with reference to FIG. 2, including, for example, constriction velocity, maximum and minimum apertures, dilation velocity, apertures and/or percentage of change. In some implementations, the pupillometry measure is determined based on the first metric and the second metric computed from the first image and the second image, respectively.

Operations of the process 500 includes generating a signal for adjusting a cardiopulmonary therapy based on the pupillometry measure (510). In some implementations, the cardiopulmonary therapy can include administering a pressure associated with intrathoracic pressure regulation (IPR). In some implementations, the cardiopulmonary therapy can include ventilation or chest compression. The IPR pressure adjustment can be substantially similar to the IPR adjustment described above with reference to FIG. 2. In some implementations, the signal for adjusting the IPR pressure can represent a pressure decrease that is held until reflected in the pupillometry measure. In some implementations, such pressure decrease can be provided in a series of 1 mm Hg increments and help unchanged between approximately ten seconds and two minutes. In some implementations, the IPR pressure can be dynamically adjusted based on pupillometry measures determined over a period of time. For example, the pupillometry measures can be determined at least every ten seconds to dynamically adjust the IPR pressure.

The signal for adjusting the cardiopulmonary therapy can include a feedback signal. The feedback signal can be used for open-loop feedback or closed-loop feedback. In one example of closed-loop feedback, the feedback signal can be provided to a device that delivers at least a portion of the cardiopulmonary therapy. For example, if the cardiopulmonary therapy includes IPR, the feedback signal can be provided to the device controlling the IPR such that the feedback signal causes adjustments in the controlling device. In one example of open-loop feedback, the feedback signal may generate an audible or visual signal that represents a feedback related to the cardiopulmonary therapy. For example, if the cardiopulmonary therapy includes manual chest compressions provided by a caregiver, the feedback signal may generate a visual display (e.g., on a display device of a mobile device, defibrillator, monitor, or another device) or sound (e.g., a verbal prompt, a tonal prompt etc.) that provides feedback information on the chest compressions being performed. The feedback information can include, for example, one or more of, information on the efficacy of the therapy, instructions for adjusting the therapy, or alerts.

Figure 6:
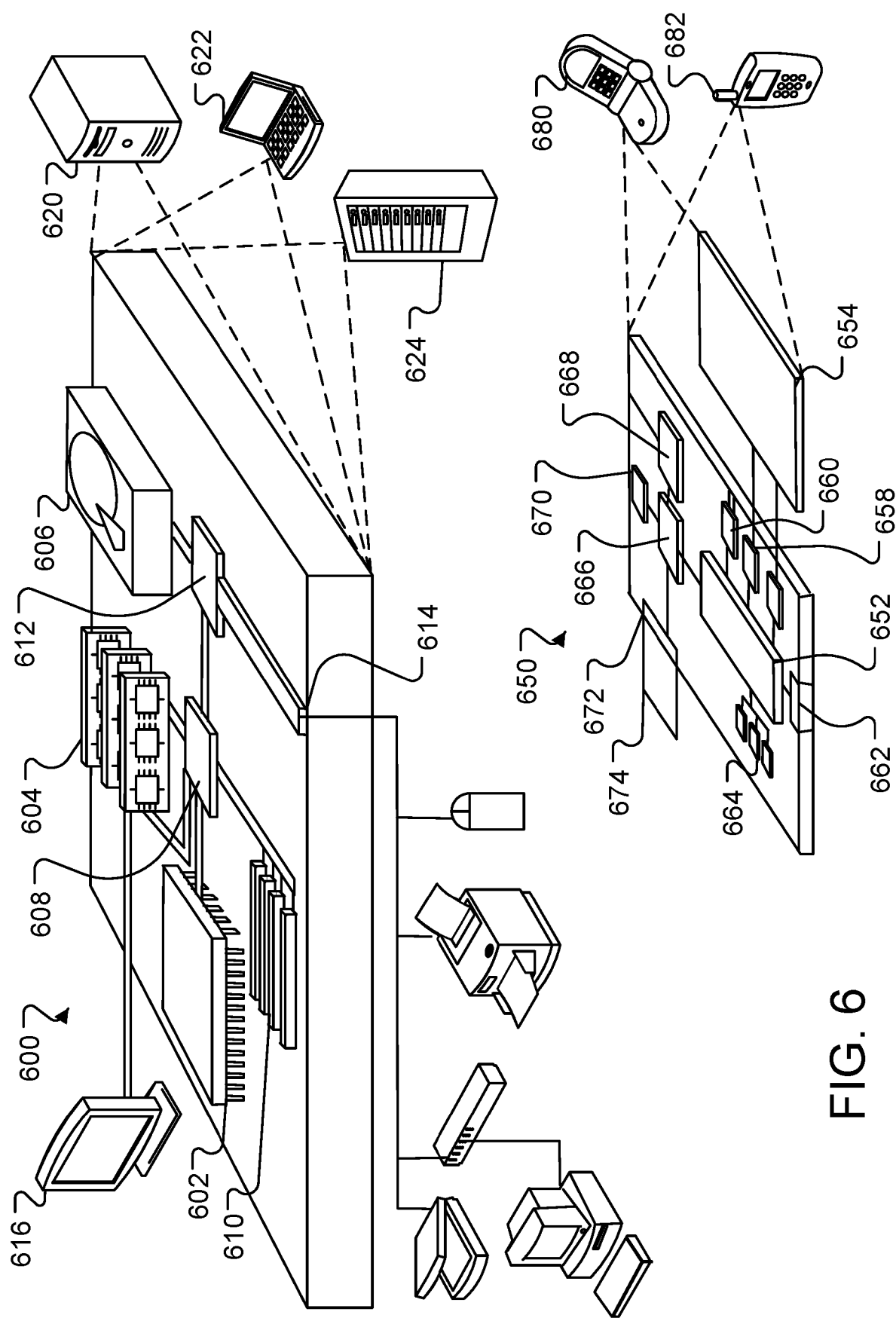
FIG. 6 is a block diagram of a computing device.

FIG. 6 shows an example of a generic computer device 600 and a generic mobile computer device 650, which may be used with the techniques described here. Computing device 600 is intended to represent various forms of digital computers, such as laptops, desktops, workstations, personal digital assistants, servers, blade servers, mainframes, and other appropriate computers. Computing device 650 is intended to represent various forms of mobile devices, such as personal digital assistants, cellular telephones, smartphones, and other similar computing devices. The components shown here, their connections and relationships, and their functions, are meant to be exemplary only, and are not meant to limit implementations of the inventions described and/or claimed in this document.

Computing device 600 includes a processor 602, memory 604, a storage device 606, a high-speed interface 608 connecting to memory 604 and high-speed expansion ports 610, and a low speed interface 612 connecting to low speed bus 614 and storage device 606. Each of the components 602, 604, 606, 608, 610, and 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as display 616 coupled to high speed interface 608. In other implementations, multiple processors and/or multiple buses may be used, as appropriate, along with multiple memories and types of memory. Also, multiple computing devices 600 may be connected, with each device providing portions of the necessary operations (e.g., as a server bank, a group of blade servers, or a multi-processor system).

The memory 604 stores information within the computing device 600. In one implementation, the memory 604 is a volatile memory unit or units. In another implementation, the memory 604 is a non-volatile memory unit or units. The memory 604 may also be another form of computer-readable medium, such as a magnetic or optical disk.

The storage device 606 is capable of providing mass storage for the computing device 600. In one implementation, the storage device 606 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 604, the storage device 606, memory on processor 602, or a propagated signal.

The high speed controller 608 manages bandwidth-intensive operations for the computing device 600, while the low speed controller 612 manages lower bandwidth-intensive operations. Such allocation of functions is exemplary only. In one implementation, the high-speed controller 608 is coupled to memory 604, display 616 (e.g., through a graphics processor or accelerator), and to high-speed expansion ports 610, which may accept various expansion cards (not shown). In the implementation, low-speed controller 612 is coupled to storage device 606 and low-speed expansion port 614. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. It may also be implemented as part of a rack server system 624. In addition, it may be implemented in a personal computer such as a laptop computer 622. Alternatively, components from computing device 600 may be combined with other components in a mobile device (not shown), such as device 650. Each of such devices may contain one or more of computing device 600, 650, and an entire system may be made up of multiple computing devices 600, 650 communicating with each other.

Computing device 650 includes a processor 652, memory 664, an input/output device such as a display 654, a communication interface 666, and a transceiver 668, among other components. The device 650 may also be provided with a storage device, such as a microdrive or other device, to provide additional storage. Each of the components 650, 652, 664, 654, 666, and 668, are interconnected using various buses, and several of the components may be mounted on a common motherboard or in other manners as appropriate.

The processor 652 can execute instructions within the computing device 650, including instructions stored in the memory 664. The processor may be implemented as a chipset of chips that include separate and multiple analog and digital processors. The processor may provide, for example, for coordination of the other components of the device 650, such as control of user interfaces, applications run by device 650, and wireless communication by device 650.

Processor 652 may communicate with a user through control interface 658 and display interface 656 coupled to a display 654. The display 654 may be, for example, a TFT LCD (Thin-Film-Transistor Liquid Crystal Display) or an OLED (Organic Light Emitting Diode) display, or other appropriate display technology. The display interface 656 may comprise appropriate circuitry for driving the display 654 to present graphical and other information to a user. The control interface 658 may receive commands from a user and convert them for submission to the processor 652. In addition, an external interface 662 may be provided in communication with processor 652, so as to enable near area communication of device 650 with other devices. External interface 662 may provide, for example, for wired communication in some implementations, or for wireless communication in other implementations, and multiple interfaces may also be used.

The memory 664 stores information within the computing device 650. The memory 664 can be implemented as one or more of a computer-readable medium or media, a volatile memory unit or units, or a non-volatile memory unit or units. Expansion memory 674 may also be provided and connected to device 650 through expansion interface 672, which may include, for example, a SIMM (Single In Line Memory Module) card interface. Such expansion memory 674 may provide extra storage space for device 650, or may also store applications or other information for device 650. Specifically, expansion memory 674 may include instructions to carry out or supplement the processes described above, and may include secure information also. Thus, for example, expansion memory 674 may be provide as a security module for device 650, and may be programmed with instructions that permit secure use of device 650. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 664, expansion memory 674, memory on processor 652, or a propagated signal that may be received, for example, over transceiver 668 or external interface 662.

Device 650 may communicate wirelessly through communication interface 666, which may include digital signal processing circuitry where necessary. Communication interface 666 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 668. In addition, short-range communication may occur, such as using a Bluetooth, WiFi, or other such transceiver (not shown). In addition, GPS (Global Positioning System) receiver module 670 may provide additional navigation- and location-related wireless data to device 650, which may be used as appropriate by applications running on device 650.

Device 650 may also communicate audibly using audio codec 660, which may receive spoken information from a user and convert it to usable digital information. Audio codec 660 may likewise generate audible sound for a user, such as through a speaker, e.g., in a handset of device 650. Such sound may include sound from voice telephone calls, may include recorded sound (e.g., voice messages, music files, etc.) and may also include sound generated by applications operating on device 650.

The computing device 650 may be implemented in a number of different forms, as shown in the figure. For example, it may be implemented as a cellular telephone 680. It may also be implemented as part of a smartphone 682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

OTHER EMBODIMENTS

Although a few implementations have been described in detail above, other modifications are possible. For example, the therapy can include delivery of chest compressions during the course of resuscitation of a patient in cardiac arrest. In such cases, the IPR device (e.g., the device 215) may be replaced or supplemented by a mechanical compression device such as the AutoPulse manufactured by ZOLL Medical of Chelmsford, Mass., or the LUCAS manufactured by Phyio-Control of Redmond, Wash. The feedback from the portable pupillometry device can then be communicated to the chest compression device to adjust its rate, depth or duty cycle of the compression. In such cases, the corresponding titration cycle can be for the compression depth, where the titration range can be 1.5-3 inches. In another example, the titration range for duty cycle can be 20%-80%. The titration range for compression rate can be in the range of 60-135 compressions per minute. In some implementations, the angle of the patient's head may be adjusted to reduce intracranial pressure during chest compressions. The adjustable therapy in this case can be the elevation angle of the head. For example, the angle of the head can be adjusted and the same titration cycle can be performed, typically over a range of 5-30 degrees. In some implementations, the angle can be automated and under the control of either the mechanical compression device or another device. Alternatively, the elevation angle can also be manually controllable by a caregiver.

In some implementations, multiple therapies may be titrated at once. For example, both compressions and IPR pressure can be titrated jointly. In such cases, the methods for titration optimization can be similar to that employed in Box-Behnken designs, i.e., experimental designs for response surface methodology.

In some implementations, the therapy can include manually delivered chest compressions where feedback (e.g., visual/audio feedback) is provided to the caregiver about the quality of the compressions. For example, a caregiver may be directed to varying levels of compression depth or rate during the titration cycle using techniques as described in U.S. Published Application 2011/0202100 A1, the entire content of which is incorporated herein by reference.

Accordingly, other implementations are within the scope of the following claims.

What is claimed is:

1. A system comprising:
one or more memory devices configured to store computer readable instructions; and
a treatment adjustment engine comprising one or more processing devices, the treatment adjustment engine configured to:
obtain a first image of an eye of a subject;
obtain a second image of the eye of the subject, wherein the second image is captured in the presence of an electronic light source;
determine, based on the first and second images, one or more metrics representing shapes of the iris and pupil in the corresponding images;
determine, based on the one or more metrics, a pupillometry measure of the subject; and
generate a signal for adjusting a cardiopulmonary therapy based on the determined pupillometry measure,
wherein the cardiopulmonary therapy comprises a pressure associated with intrathoracic pressure regulation (IPR), and
wherein the signal for adjusting the cardiopulmonary therapy represents a pressure decrease that is held until reflected in the pupillometry measure.

2. The system of claim 1, wherein in the pressure decrease is provided in a series of 1 mmHg increments.

3. The system of claim 1, wherein the pressure decrease is held between approximately ten seconds and two minutes.

4. The system of claim 1, wherein obtaining the first image further comprises:
presenting, on a display device, user interface that includes a graphical element for specifying boundaries for the first image; and
generating a control signal for an imaging device to capture the first image based on a user-input received via the user interface.

5. The system of claim 1, wherein obtaining the second image further comprises:
presenting, on a display device, a user interface that includes a graphical element for specifying an area of the eye to be included in the second image;
generating a first control signal for activating the electronic light source; and
generating a second control signal for an imaging device to capture the second image based on a user-input received via the user interface.

6. The system of claim 1, wherein determining the one or more metrics comprises determining a first metric as a function of (i) iris area and (ii) pupil area as captured in the first image.

7. The system of claim 6, further comprising determining a second metric as a function of (i) iris area and (ii) pupil area as captured in the second image.

8. The system of claim 7, wherein the pupillometry measure is determined based on the first metric and the second metric.

9. The system of claim 1, wherein the cardiopulmonary therapy comprises at least one of ventilation or chest compression.

10. The system of claim 1, wherein the signal for adjusting the cardiopulmonary therapy comprises a feedback signal.

11. The system of claim 10, wherein the feedback signal causes an adjustment in a device delivering at least a portion of the cardiopulmonary therapy.

12. The system of claim 1, wherein the signal for adjusting the cardiopulmonary therapy comprises an audible or visual signal representing a feedback related to the cardiopulmonary therapy.

13. A method comprising:
    obtaining a first image of an eye of a subject;
    obtaining a second image of the eye of the subject, wherein the second image is captured in the presence of an electronic light source;
    determining, based on the first and second images, one or more metrics representing the shapes of the iris and pupil in the corresponding images;
    determining, based on the one or more metrics, a pupillometry measure of the subject; and
    generating a signal for adjusting a cardiopulmonary therapy based on the determined pupillometry measure,
    wherein the cardiopulmonary therapy comprises a pressure associated with intrathoracic pressure regulation (IPR), and
    wherein at least one of:
        the signal for adjusting the cardiopulmonary therapy represents a pressure decrease that is held until reflected in the pupillometry measure, or
        the pressure associated with IPR is dynamically adjusted based on pupillometry measures determined over a period of time.

14. A system comprising:
    one or more memory devices configured to store computer readable instructions; and
    a treatment adjustment engine comprising one or more processing devices, the treatment adjustment engine configured to:
        obtain a first image of an eye of a subject;
        obtain a second image of the eye of the subject, wherein the second image is captured in the presence of an electronic light source;
        determine, based on the first and second images, one or more metrics representing shapes of the iris and pupil in the corresponding images;
        determine, based on the one or more metrics, a pupillometry measure of the subject; and
        generate a signal for adjusting a cardiopulmonary therapy based on the determined pupillometry measure,
    wherein the cardiopulmonary therapy comprises a pressure associated with intrathoracic pressure regulation (IPR), and
    wherein the treatment adjustment engine operates in a repetitive manner to dynamically adjust the pressure associated with IPR based on pupillometry measures determined over a period of time.

15. The system of claim 14, wherein the pupillometry measure is determined at least every ten seconds to dynamically adjust the pressure associated with IPR.

16. The system of claim 14, wherein obtaining the first image further comprises:
    presenting, on a display device, user interface that includes a graphical element for specifying boundaries for the first image; and
    generating a control signal for an imaging device to capture the first image based on a user-input received via the user interface.

17. The system of claim 14, wherein obtaining the second image further comprises:
    presenting, on a display device, a user interface that includes a graphical element for specifying an area of the eye to be included in the second image;
    generating a first control signal for activating the electronic light source; and
    generating a second control signal for an imaging device to capture the second image based on a user-input received via the user interface.

18. The system of claim 14, wherein determining the one or more metrics comprises determining a first metric as a function of (i) iris area and (ii) pupil area as captured in the first image.

19. The system of claim 18, further comprising determining a second metric as a function of (i) iris area and (ii) pupil area as captured in the second image.

20. The system of claim 19, wherein the pupillometry measure is determined based on the first metric and the second metric.

21. The system of claim 14, wherein the cardiopulmonary therapy comprises at least one of ventilation or chest compression.

22. The system of claim 14, wherein the signal for adjusting the cardiopulmonary therapy comprises a feedback signal.

23. The system of claim 22, wherein the feedback signal causes an adjustment in a device delivering at least a portion of the cardiopulmonary therapy.

24. The system of claim 14, wherein the signal for adjusting the cardiopulmonary therapy comprises an audible or visual signal representing a feedback related to the cardiopulmonary therapy.

* * * * *